US007664223B1

(12) United States Patent
Danielsson et al.

(10) Patent No.: US 7,664,223 B1
(45) Date of Patent: Feb. 16, 2010

(54) COLLIMATOR ELEMENT

(75) Inventors: Mats Danielsson, Täby (SE); Theresa Lammroth, Stockholm (SE); Lénnart Rapp, Malmö (SE)

(73) Assignee: Sectra Mamea AB, Kista (SE)

( * ) Notice: Subject to any disclaimer, the term of this patent is extended or adjusted under 35 U.S.C. 154(b) by 1810 days.

(21) Appl. No.: 09/683,769

(22) Filed: Feb. 12, 2002

Related U.S. Application Data

(60) Provisional application No. 60/268,156, filed on Feb. 12, 2001.

(51) Int. Cl.
*A61B 6/04* (2006.01)

(52) U.S. Cl. .......................................... 378/37; 378/46

(58) Field of Classification Search .................. 378/28, 378/34, 35, 36, 37–46
See application file for complete search history.

(56) References Cited

U.S. PATENT DOCUMENTS 4,203,037 A * 5/1980 Gur et al. ...................... 378/37
4,375,695 A * 3/1983 Harding et al. ................ 378/6
4,389,729 A * 6/1983 Stein ......................... 378/98.2
4,493,098 A * 1/1985 Riihimaki et al. ........... 378/146
5,627,869 A 5/1997 Andrew et al. ................ 378/37
6,115,447 A * 9/2000 Hsieh .......................... 378/19
6,175,609 B1 * 1/2001 Edic et al. ...................... 378/7

FOREIGN PATENT DOCUMENTS

EP 0 417 965 A2 3/1991
EP 0 417 965 A3 3/1991
EP 0 426 285 A1 5/1991
EP 1 120 086 A1 8/2001
JP 0553610 U 7/1993
JP 8112272 A 5/1996
JP 9168537 A 6/1997
WO WO 98/49939 A1 11/1998

* cited by examiner

*Primary Examiner*—Max Noori
(74) *Attorney, Agent, or Firm*—Novak Druce + Quigg LLP

(57) ABSTRACT

A beam collimator arrangement for scanned-slot x-ray imaging having one or several collimators in an x-ray apparatus is disclosed. The beam collimator arrangement includes an x-ray source; an x-ray image receiver positioned to receive x-rays from the x-ray source; a compressor or means for compressing a female breast to be examined where the compressor is positionable between the x-ray source and the x-ray image receiver; and the beam collimator is positioned between the x-ray source and the compressor. The beam collimator arrangement is arranged on a carrying structure to displace the beam collimator arrangement between a first position when no x-ray exposure is conducted and a second position before x-ray exposure is initiated.

4 Claims, 3 Drawing Sheets

21
20
P
22
27
A
22
23
26
24
25

COLLIMATOR ELEMENT

CROSS REFERENCE TO RELATED APPLICATIONS

The present application claims the benefit of U.S. Provisional Application No. 60/268,156 filed 12 Feb. 2001.

BACKGROUND OF INVENTION

1. Technical Field

The present invention relates to scanned-slit x-ray imaging in mammography wherein for the first time a high spatial resolution image can be registered without compromising the agronomy in positioning the breast. It further relates to a beam collimator arrangement consisting of one or several collimators in an x-ray apparatus shaping the x-ray beam to hit the active detector area (pre-collimator) and to remove scattered x-rays (aft collimator).

2. Background Information

When carrying out scanned-slit mammography, one critical problem is placing the breast of a patient in the correct position while at the same time also positioning the moving collimator as close as possible to the breast in order to obtain a high quality image with respect to spatial resolution.

FIG. 1*a* provides a schematic side view of a digital mammography x-ray equipment 10 having an x-ray source 11, a collimator arrangement 12, compression paddles 13 and 14, and a detector assembly 15. X-rays are denoted with 17. The breast 16 to be examined (x-rayed) is placed between the compression paddles 13 and 14 and exposed to pressure. This pressure prevents motion during the exposure, and also decreases the amount of overlapping tissue since the breast is flattened out.

As illustrated in FIGS. 1*a* and 1*b*, the collimator arrangement 12 must be placed as close as possible to the upper compression paddle 12. As indicated in FIG. 1*a*, the image quality is compromised if this does not happen. This is because the size of the x-ray source imaged on the detector through the slit the spatial resolution b1 will deteriorate if the collimator is moved away from the object. This is only true is one dimension—the dimension orthogonal to the slit as indicated in FIG. 1*b*. Thus, when placing the breast in the examining position one must avoid the collimator arrangement, and when the examining starts the collimator must be placed as close as possible to the breast above the upper paddle.

European Patent No. 0417965 discloses a method and apparatus for improving imaging in an X-ray mammography machine having a controllable X-ray source. The invention incorporates apparatus for directing the X-ray beam in a preselected configuration onto at least a portion of a target area. The intensity of the beam created is detected in each of a plurality of substantially equal segments of the target area and a first segment of lowest radiation intensity is identified. The X-ray source is adjusted to establish a predetermined radiation intensity in the identified first segment. Second segments are then identified each having a radiation intensity greater than a predetermined percentage of the radiation intensity in the identified first segment. The radiation intensity directed toward the identified second segments is then automatically attenuated by a control system responsive to the radiation intensity detected in the second segments. The attenuation is achieved by moving collimators into the beam so as to reduce the radiation directed towards the second segments. The beam is scanned over the target and continuously adjusted in accordance with the radiation detected in each of the segments of the beam. In this manner, each area of the target receives just sufficient radiation to provide proper imaging without overexposing area of the target, which have less attenuation than other areas. Thus, the object of this invention is to obtain attenuation by horizontally displacing the collimator.

A mammography apparatus for obtaining mammography images with optimal beam collimation is disclosed in U.S. Pat. No. 5,627,869. Proportional control of collimator element position based upon compression paddle position and dimension inputs is provided to obtain optimal collimation of the X-ray beam for a desired imaging technique and compressed breast thickness. Relevant objects of this invention include providing a mammography apparatus with an X-ray beam collimator that is automatically adjusted to provide an appropriately collimated X-ray beam for any magnification factor, and to provide a mammography apparatus with an X-ray beam collimator that is automatically adjusted, thereby providing an X-ray beam that is appropriately collimated for any magnification factor for a breast of any thickness using a compression paddle of any dimension. As such, the collimator is provided with collimator blades that are controlled so as to be displaced in horizontal direction.

U.S. Pat. No. 4,203,037 discloses an apparatus for exposing an object to x-ray radiation. The apparatus includes an adjustable object supporting and compressing means, and a first collimator means having an opening and that is disposed between the x-ray generator and the object supporting means. A second collimator means having an opening and that is disposed between the object supporting means and x-ray detecting means is also provided. Means are provided for moving the first and second collimator means so that the alignment between the openings therein and the x-ray generator is maintained. This is done in order to expose portions of the object passing through the first collimator means in a sequential fashion while being x-rayed, and permit the x-ray to pass through the opening in the second collimator means and impinge upon the x-ray detecting means. The object supporting and compressing means is preferably structurally independent of the collimator means. The x-ray detecting means preferably takes the form of a highly sensitive detector such as a film-screen cassette or a self-scanning array of photodiodes optically coupled to a scintillator means.

SUMMARY OF INVENTION

The present invention includes an x-ray source; an x-ray image receiver positioned to receive x-rays from the x-ray source; a positioner or means for positioning the object to be examined, the positioner being between the x-ray source and the x-ray image receiver; and a pre-collimator positioned between the x-ray source and the positioner for positioning the object.

Thus, the present invention provides a collimator arrangement and an x-ray apparatus employing such a collimator arrangement that solves the problems associated with the prior art while providing the nurse or other personnel a working field that is free from obstacles. The present invention also provides a collimator arrangement that can be placed as close as possible to the object examined during exposure.

The collimator arrangement of the present invention is arranged on a carrying structure to displace the beam collimator arrangement between a first position when no x-ray exposure is conducted and a second position right before x-ray exposure is initiated and during the x-ray exposure. Preferably, the second position is in a substantially short distance from said compressing means. For flexibility, the displacement is in the lateral and/or horizontal direction.

The invention also relates to a mammography apparatus having an X-ray source; and X-ray image receiver positioned to receive X-rays from the X-ray source; first and second compressors or means for compressing tissue, the compressors or means being positionable between the X-ray source and the X-ray image receiver and wherein the compressors or means further provide a compression surface of predetermined dimensions; a beam collimator positioned between the X-ray source and the means for compressing tissue. The apparatus further includes a displacer or means for displacing the beam collimator arrangement between a first position when no x-ray exposure is conducted and a second position before x-ray exposure is initiated.

BRIEF DESCRIPTION OF DRAWINGS

In the following, the invention will be further described in a non-limiting way with reference to the accompanying drawings in which.

DETAILED DESCRIPTION

Figure 1A:
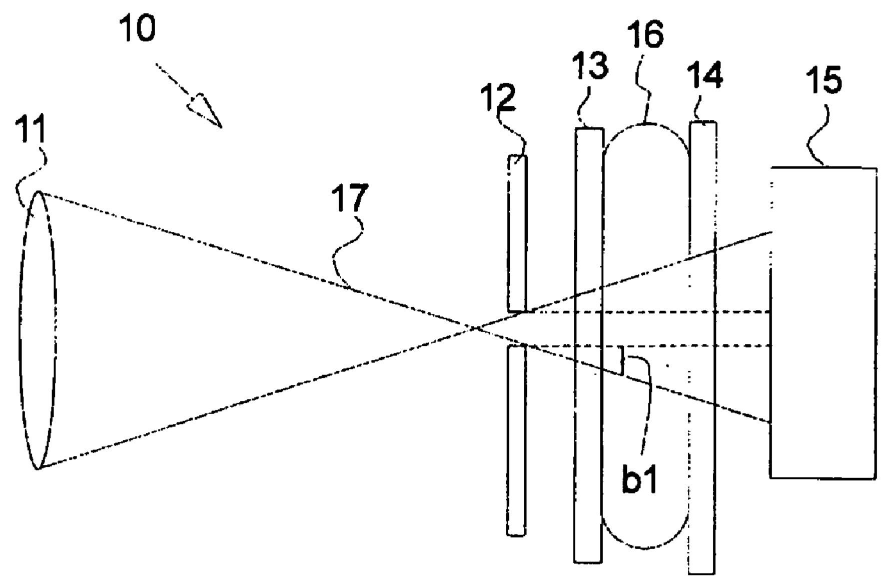
FIGS. 1*a* and 1*b* are schematic illustrations of an x-ray apparatus as known in the art.
Figure 1B:
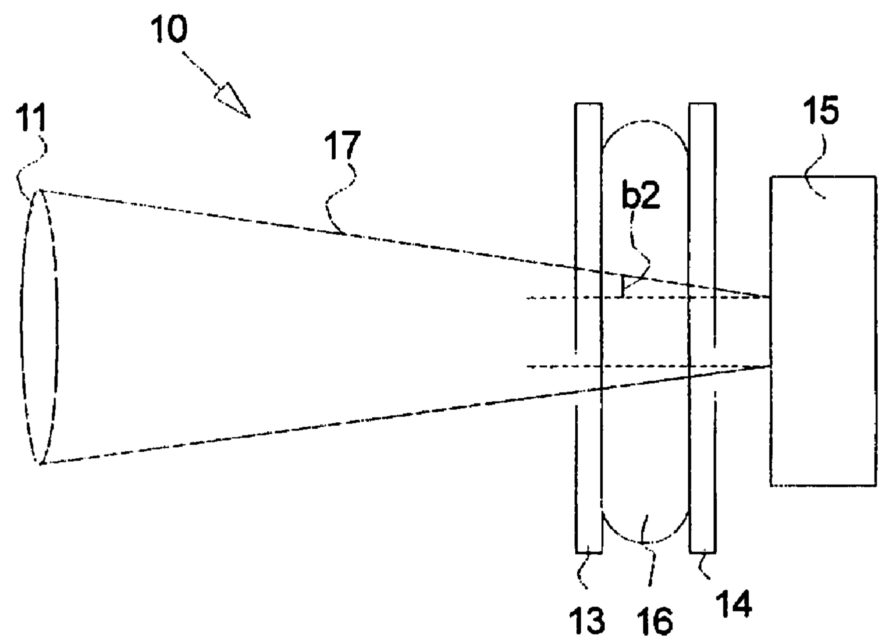
Figure 2:
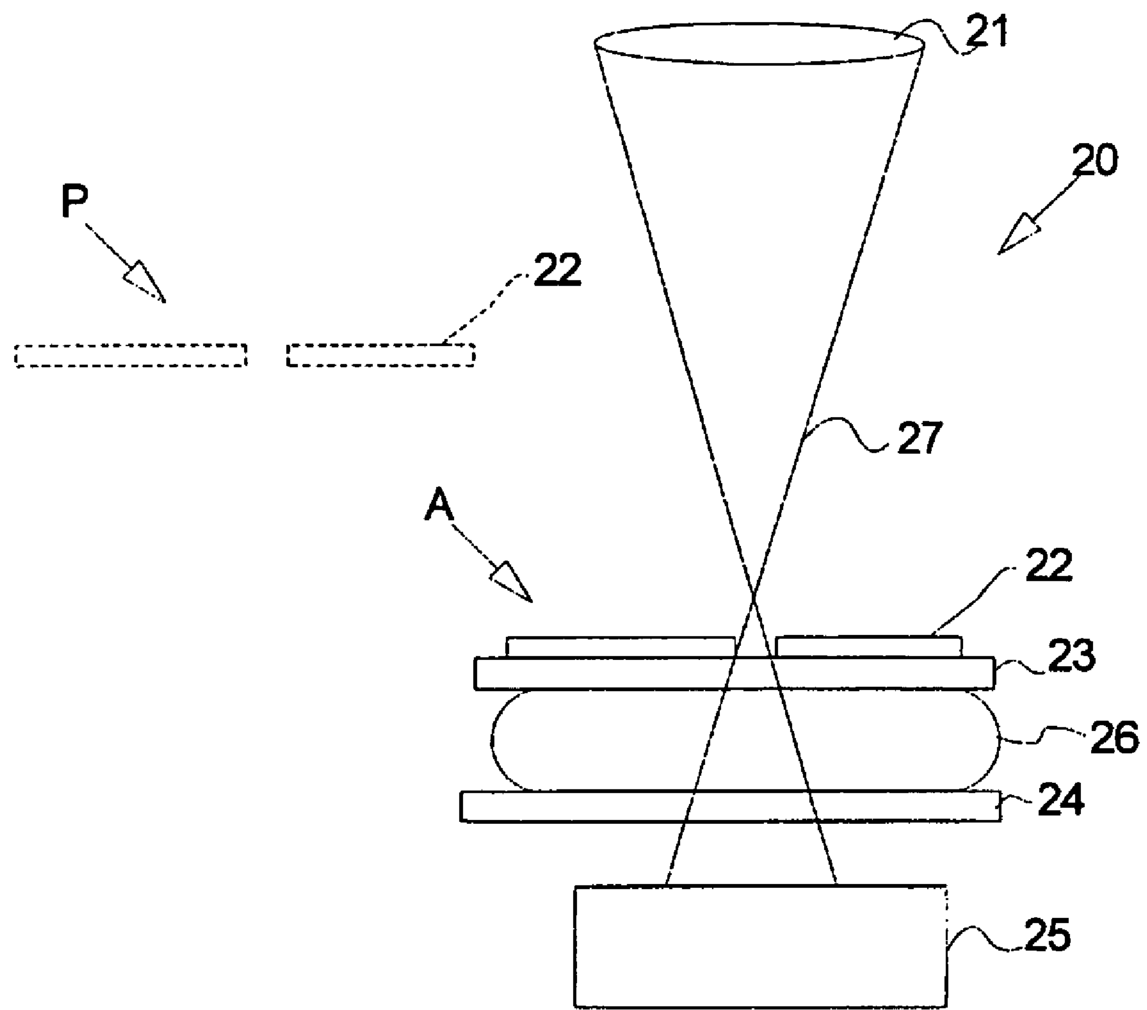
FIG. 2 illustrates in a schematic way an embodiment of an x-ray apparatus according to the present invention.

FIG. 2 is a schematic view illustrating an x-ray apparatus 20 according to the present invention. The apparatus 20 includes an x-ray source 21, a collimator arrangement 22, compression paddles 23 and 24, and a detector assembly 25. The breast 26 to be examined (x-rayed) is placed between the compression paddles 23 and 24 and exposed to a pressure that flattens it so that as much as possible of the breast is exposed to the x-rays and detected by the detector assembly 25 and a sufficient contrast is obtained. The x-rays are denoted with 27.

The collimator arrangement 22 is arranged to assume at least two positions, a parking position P and an active position A. In the parking position, the collimator is arranged in an area that does not interfere with the positioning of the patient's breast between the compression paddles. This area can be an area outside the exposure area, preferably by displacing and/or lifting the collimator arrangement from the exposure area. Displacement of the entire collimator arrangement is a lateral movement while the lifting is a vertical movement with respect to the plane of the drawing.

When the examination starts, the collimator arrangement 22 is placed in the parking position P. It must be high enough or offset enough so as to not disturb the nurse's adjustment of the breast 26. When the compression is completed and the exposure to x-ray is to be initiated, the collimator arrangement 22 moves downwards/sideways and stops in a position as close as possible to the compression plate 23. When the exposure is completed, the collimator arrangement moves upwards/sideways with at least the speed of the compression plate to the parking position. The collimator motion towards the compression paddles can be initiated, e.g., by a dedicated switch after the positioning of the breast is carried out. It is important that the time the breast is compressed is minimized. For this reason, the movement of the collimator arrangement should be as fast as possible without causing patient anxiety. An exact parking position for the collimator can be configured with the use of commands of a control system between approximately 18 cm from detector and approximately 50 cm from the detector. In particular, when multi-slits collimators are used, it is important that the collimator is placed close to the object to be examined. In this case, the resolution of the resultant image is deteriorated in a direction perpendicular to the collimator's slits.

Figure 3:
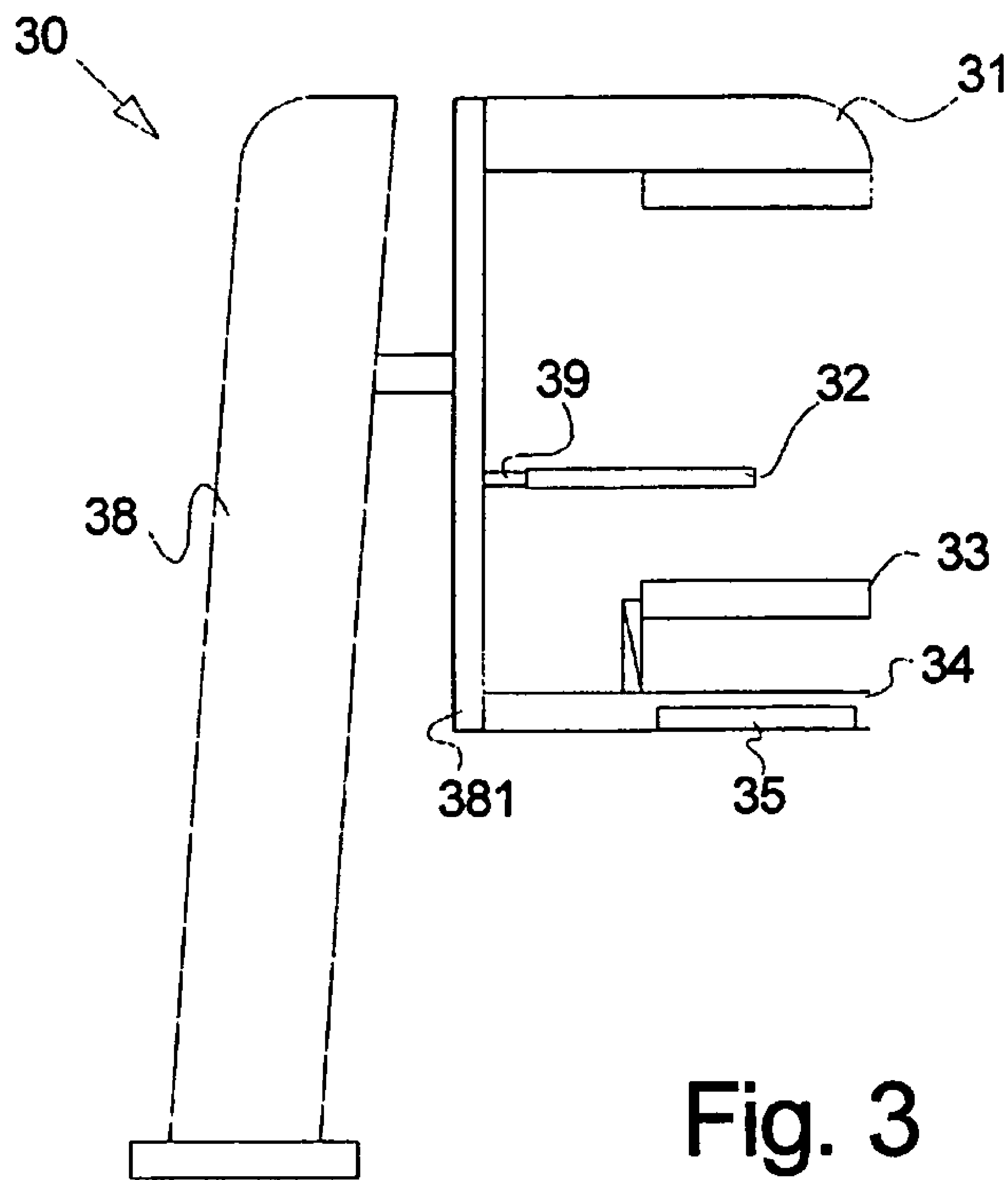
FIG. 3 illustrates in a schematic way a more detailed embodiment of an x-ray apparatus according to the present invention.

FIG. 3 is a schematic and more detailed illustration of an x-ray apparatus 30 according to the invention. The apparatus 30 generally comprises a base 38, an imaging arm 381 pivotally attached to the base 38, an x-ray source 31 fixed to one end of the imaging arm 381, an image receiver or detector assembly 35 fixed at a second end of the imaging arm. The apparatus also includes compression paddle holders, which are slidably attached to the imaging arm. The compression paddle holder holds upper and lower compression paddles 33 and 34, respectively. A displaceable collimator arrangement 32 is arrange on a collimator arm 39. According to this embodiment, the detector assembly 35 is integrated with the lower compression paddle 34.

The collimator holder arm 39 is arranged to displace the collimator arrangement 32 by sliding the collimator in a vertical direction and also it can comprise a telescopic structure to displace the collimator arrangement horizontally. In FIG. 3, the collimator arrangement 32 is situated in its parking position.

The invention is not limited to mammography and can be used in any type of x-ray imaging apparatuses, using semi-conducting or gaseous detectors or x-ray film.

The invention is not limited to the shown embodiments, but can be varied in a number of ways without departing from the scope of the appended claims. The arrangement and method can be implemented in various ways depending on the application, functional units, needs and requirements, and so forth.

The invention claimed is:

1. A beam collimator arrangement for scanned-slot mammography comprising at least one collimator in an x-ray apparatus, said apparatus comprising:

an x-ray source;

an x-ray image receiver positioned to receive x-rays from the x-ray source;

a compressor for compressing a female breast to be examined, said compressor being positionable between the x-ray source and the x-ray image receiver; and a beam collimator positioned between the x-ray source and the compressor for compressing tissue, said beam collimator arrangement being arranged on a carrying structure that displaces the beam collimator arrangement between a first position when no x-ray exposure is conducted and a second position before x-ray exposure is initiated, and wherein said first position is vertically and horizontally displaced with respect to the second position.

2. The beam collimator arrangement of claim 1, wherein said second position is within a substantially short distance from said compressor.

3. The beam collimator arrangement of claim 1, wherein said first position is located vertically above the second position.

4. A mammography apparatus comprising:

an X-ray source;

an X-ray image receiver positioned to receive X-rays from the X-ray source;

first and second means for compressing tissue, the means being positionable between the X-ray source and the X-ray image receiver and wherein the means further providing a compression surface of predetermined dimensions;

a beam collimator positioned between the X-ray source and the means for compressing tissue; characterized in that said apparatus further comprises means for displacing said beam collimator arrangement to displace the beam collimator arrangement between a first position when no x-ray exposure is conducted and a second position before x-ray exposure is initiated and that the first position is vertically and horizontally displaced with respect to said second position.

* * * * *